United States Patent
Jugl et al.

(10) Patent No.: US 12,226,618 B2
(45) Date of Patent: Feb. 18, 2025

(54) DRIVE TRAIN FOR DIAL OF A TORSION-SPRING ASSISTED WIND-UP INJECTION DEVICE

(71) Applicant: SANOFI, Paris (FR)

(72) Inventors: Michael Jugl, Frankfurt am Main (DE); Matthew Meredith Jones, Warwick (GB); Axel Teucher, Frankfurt am Main (DE); Stefan Blancke, Frankfurt am Main (DE); Ralph Donald Quentin Collings, Bristol (GB); James Robert Coop, Bristol (GB); James Anthony West, Bristol (GB); Stephen Francis Gilmore, Bristol (GB); Daniel David Higgins, Bristol (GB); Mark Digby Teucher, Bristol (GB)

(73) Assignee: SANOFI, Paris (FR)

(*) Notice: Subject to any disclaimer, the term of this patent is extended or adjusted under 35 U.S.C. 154(b) by 1197 days.

(21) Appl. No.: 16/979,629

(22) PCT Filed: Mar. 11, 2019

(86) PCT No.: PCT/EP2019/055948
§ 371 (c)(1),
(2) Date: Sep. 10, 2020

(87) PCT Pub. No.: WO2019/175072
PCT Pub. Date: Sep. 19, 2019

(65) Prior Publication Data
US 2021/0038824 A1    Feb. 11, 2021

(30) Foreign Application Priority Data
Mar. 13, 2018    (EP) .................................. 18305261

(51) Int. Cl.
A61M 5/31     (2006.01)
A61M 5/20     (2006.01)
A61M 5/315    (2006.01)

(52) U.S. Cl.
CPC ...... *A61M 5/31551* (2013.01); *A61M 5/2033* (2013.01); *A61M 5/31536* (2013.01);
(Continued)

(58) Field of Classification Search
CPC .. A61M 2005/2418; A61M 2005/3143; A61M 5/3155; A61M 5/31536; A61M 2204/42
See application file for complete search history.

(56) References Cited

U.S. PATENT DOCUMENTS

2014/0350478 A1* 11/2014 Hansen ............. A61M 5/31593
604/207
2015/0030372 A1   1/2015 Tani
(Continued)

FOREIGN PATENT DOCUMENTS

EP    0897728    2/1999
JP    H11-104240 4/1999
(Continued)

OTHER PUBLICATIONS

PCT International Preliminary Report on Patentability in International Appln. No. PCT/EP2019/055948, dated Sep. 15, 2020, 8 pages.
(Continued)

*Primary Examiner* — Courtney B Fredrickson
(74) *Attorney, Agent, or Firm* — Bond, Schoeneck & King, PLLC

(57) ABSTRACT

A drive train for a wind-up injection device, comprises a torsional energy storage adapted to be loaded or unloaded by a rotatable element, a rotatable user handle coupled with a button, a rotationally drivable expelling mechanism, and a (Continued)

clutch element coupled with the torsional energy storage via the rotatable element and comprising a ratchet for maintaining the rotatable element at one of a number of discrete angular positions, wherein via the rotatable element, the clutch element is adapted to transmit a torque from the user handle to the torsional energy storage or from the torsional energy storage to the expelling mechanism, and wherein the ratchet is switchable from one position to an adjacent position by a torque transmitted from the user handle to the torsional energy storage, and wherein the drive train is adapted to dampen torque peaks by a flexible impact portion in the area of the clutch element.

20 Claims, 14 Drawing Sheets

(52) U.S. Cl.
CPC .... *A61M 5/31541* (2013.01); *A61M 5/31586* (2013.01); *A61M 2205/42* (2013.01); *A61M 2205/581* (2013.01); *A61M 2205/582* (2013.01)

(56) References Cited

U.S. PATENT DOCUMENTS

| | | | |
|---|---|---|---|
| 2015/0265771 A1* | 9/2015 | Holtwick | A61M 5/3155 604/209 |
| 2016/0030681 A1* | 2/2016 | Jones | A61M 5/31528 604/189 |
| 2016/0287806 A1 | 10/2016 | Kraft et al. | |

FOREIGN PATENT DOCUMENTS

| | | |
|---|---|---|
| JP | 2015-534837 | 12/2015 |
| JP | 2016-540553 | 12/2016 |
| JP | 2018-501915 | 1/2018 |
| WO | WO 2014/060369 | 4/2014 |
| WO | WO 2015/071210 | 5/2015 |
| WO | WO 2016/116432 | 7/2016 |
| WO | WO 2017/158033 | 9/2017 |

OTHER PUBLICATIONS

PCT International Search Report and Written Opinion in International Appln. No. PCT/EP2019/055948, dated Apr. 16, 2019, 10 pages.

* cited by examiner

DRIVE TRAIN FOR DIAL OF A TORSION-SPRING ASSISTED WIND-UP INJECTION DEVICE

CROSS REFERENCE TO RELATED APPLICATIONS

The present application is the national stage entry of International Patent Application No. PCT/EP2019/055948, filed on Mar. 11, 2019, and claims priority to Application No. EP 18305261.2, filed on Mar. 13, 2018, the disclosures of which are incorporated herein by reference.

TECHNICAL FIELD

The disclosure generally relates to a dial mechanism for a torsion-spring assisted wind-up injection device.

BACKGROUND

From the state of the art, wind-up injection devices are known where a torque applied by the user upon a user handle such as a rotatable dial grip is transferred along a drive train to wind up and/or wind down a rotational energy storage unit such as a torsion spring. The rotational energy storage unit drives a rotationally drivable expelling mechanism. When the rotational energy storage is released, a drug dose corresponding to the accumulated rotational energy is delivered.

It is further known that the drive train may comprise a ratchet for maintaining a rotatable element at one of a number of discrete angular positions against the torque load of the rotational storage unit, whereby the ratchet is switchable from one position to an adjacent position by application of a torque to the user handle.

SUMMARY

The present disclosure relates to a drive train for a wind-up injection device driven by torsional energy storage with a smoothened rotational dialing and with an improved maintaining of a dialled dose. The present disclosure also relates to a wind-up injection device with such a drive train and a process for manufacturing such a drive train.

According to the disclosure, a drive train for a wind-up injection device for injecting a liquid drug is provided, which comprises a torsional energy storage adapted to be loaded or unloaded by a rotatable element, a rotatable user handle coupled with a button, a rotationally drivable expelling mechanism adapted to expel the liquid drug and a clutch element coupled with the torsional energy storage via the rotatable element and comprising a ratchet for maintaining the rotatable element at one of a number of discrete angular positions against the torque of the torsional energy storage, wherein the clutch element is adapted to transmit a torque from the user handle via the rotatable element to the torsional energy storage or alternatively from the torsional energy storage via the rotatable element to the expelling mechanism, and wherein the ratchet is switchable from one position to an adjacent position by a torque transmitted from the user handle to the torsional energy storage, and wherein the drive train is adapted to dampen torque peaks by a flexible impact portion in the area of the clutch element.

The solution allows softening a possible impact between the clutch element and the drivable expelling mechanism, e.g. a drive sleeve.

In an embodiment, the clutch element comprises a cylindrical clutch section and a clutch plate which radially protrudes outwards from the clutch section.

In a possible embodiment, the flexible impact portion is formed as a compressible portion arranged in an area of an axial bearing between the clutch element and the button. In particular, the flexible impact portion, e.g. the compressible portion, may be arranged between the clutch plate and the trigger button. For example, the flexible impact portion is formed as a compressible portion formed into the cylindrical clutch section of the clutch element.

According to the disclosure, the flexible impact portion may be configured as at least one recess or fold inserted into the cylindrical clutch section. In particular, the at least one, e.g. inward curved, recess or fold may be inserted into an upper clutch area of the cylindrical clutch section which extends from the clutch plate. For example, the cylindrical clutch section extends from the clutch plate towards a button, e.g. a trigger button which is distally arranged onto the device, e.g. onto the clutch element and/or the handle.

In further embodiment, the flexible impact portion is configured as at least a flexible metal element arranged in the area of the ratchet, in particular between the clutch element and the drivable expelling mechanism.

According to the disclosure, the flexible metal element may be configured to apply a spring force when the clutch element and the drivable expelling mechanism contact. The contact between the clutch element and the drivable expelling mechanism may be only occurred midway through or during tooth engagement of teeth of the clutch element and teeth of the drivable expelling mechanism, e.g. teeth of the drive sleeve. The spring force is configured low in comparison to other spring elements of the device and is configured to minimize impact on clutch holding torque.

In an exemplary embodiment, the flexible metal element may be formed as a spring having a flexible ramped profile acting axially and/or tangentially between the clutch element and the drivable expelling mechanism. The flexible ramped profile does not resist tangential motion in the dose selection direction.

In particular, the flexible metal element is formed as a spring element having at least two protruding spring ramp elements. For instance, the spring element may be formed as a washer with protruding flexible clamping portions and/or spring portions. The clamping portion serves as holding elements to hold the flexible metal element onto the clutch element. The flexible spring portion, e.g. a spring ramp, serves as damper and acts axially and/or tangentially for slowing a contact speed in correction direction of the handle. In a possible embodiment, the flexible metal element may be configured as a partially or fully collared disc with upstanding spring elements, e.g. spring hooks and/or spring clamps serving as holding elements as well as damping elements.

According to the disclosure, the flexible impact portion may be configured as at least a compressible portion of the drivable expelling mechanism.

For example, the compressible portion of the drivable expelling mechanism is arranged in the area of the ratchet, in particular between the clutch element and the drivable expelling mechanism.

According to an exemplary embodiment, the compressible portion of the drivable expelling mechanism is configured as a slot in an edge region of the drivable expelling mechanism. In particular, the slot is inserted into the drivable expelling mechanism beneath protruding teeth of the drivable expelling mechanism. The slot may be inserted for instance in an upper edge region of the drivable expelling mechanism which, in assembled state, is arranged beneath teeth of the clutch element Further, the slot may be configured so that, due to impact onto the teeth, the teeth of the drivable expelling mechanism deflects.

According to the disclosure, the flexible impact portion is formed as a compressible pad arranged onto the clutch plate of the clutch element.

According to an exemplary embodiment, the flexible impact portion is configured as compressible nose extended from the rotatable element.

Further, a wind-up injection device comprises a drive train described above.

In an exemplary embodiment, the torsional energy storage comprises a torsional spring formed as a spiral spring or as a helical spring.

In an embodiment of the disclosure, the torsional energy storage comprises a compression spring and a gear element adapted to transform a translation into a rotation, wherein the translational side of the gear element is coupled to the compression spring and wherein the rotational side of the gear element is coupled to the clutch element.

As an advantage, a cost-effective manufacturing of the drive train is possible.

The drug delivery device, as described herein, may be configured to inject a drug or medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector.

The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 5 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge. The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may be activated via an activation mechanism. Such an activation mechanism can include one or more of a button, a lever, a needle sleeve, or other activation component. Activation may be a one-step or multi-step process. That is, a user may need to activate one or more activation mechanism in order to cause the automated function. For example, a user may depress a needle sleeve against their body in order to cause injection of a medicament. In other devices, a user may be required to depress a button and retract a needle shield in order to cause injection.

In addition, such activation may activate one or more mechanisms. For example, an activation sequence may activate at least two of needle insertion, medicament injection, and needle retraction. Some devices may also require a specific sequence of steps to cause the one or more automated functions to occur. Other devices may operate with sequence independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE FIGURES

The present disclosure will become fully understood from the detailed description given below and the accompanying drawings, which are given by way of illustration only, and do not limit the present disclosure, and wherein.

Corresponding parts are marked with the same reference symbols in all figures.

DETAILED DESCRIPTION

Figure 1:
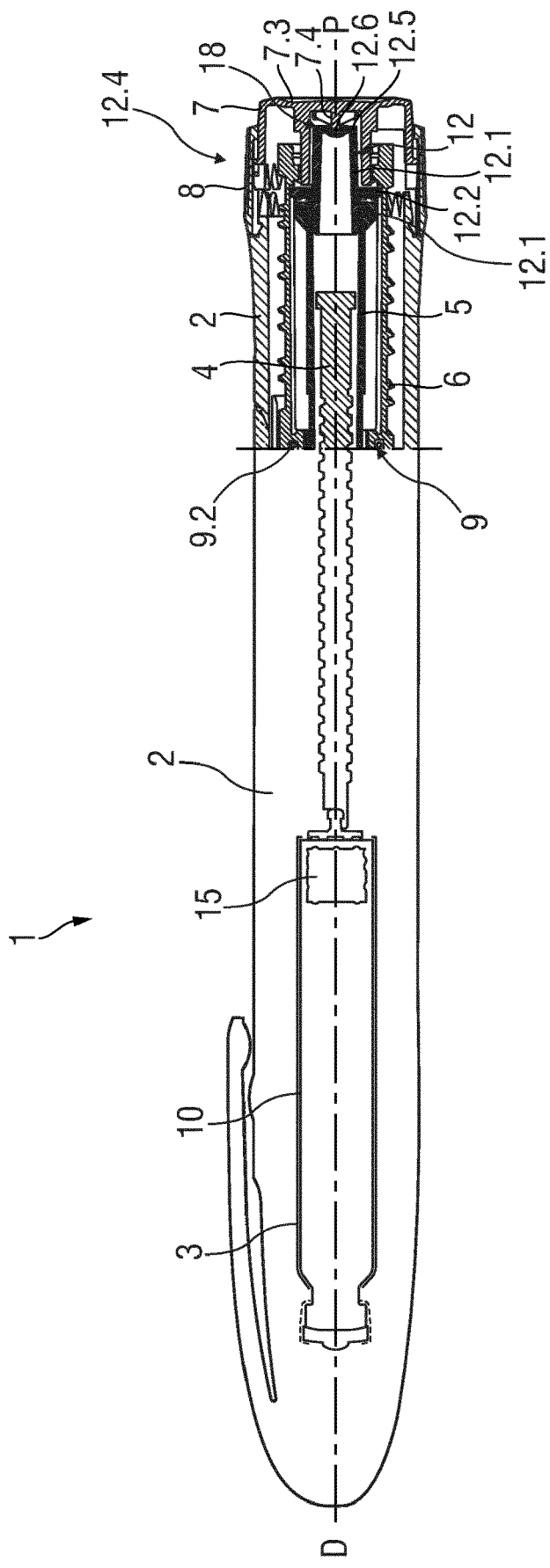
FIG. 1 is a schematic longitudinal section of an exemplary embodiment of a wind-up injection device according to prior art.
Figure 2:
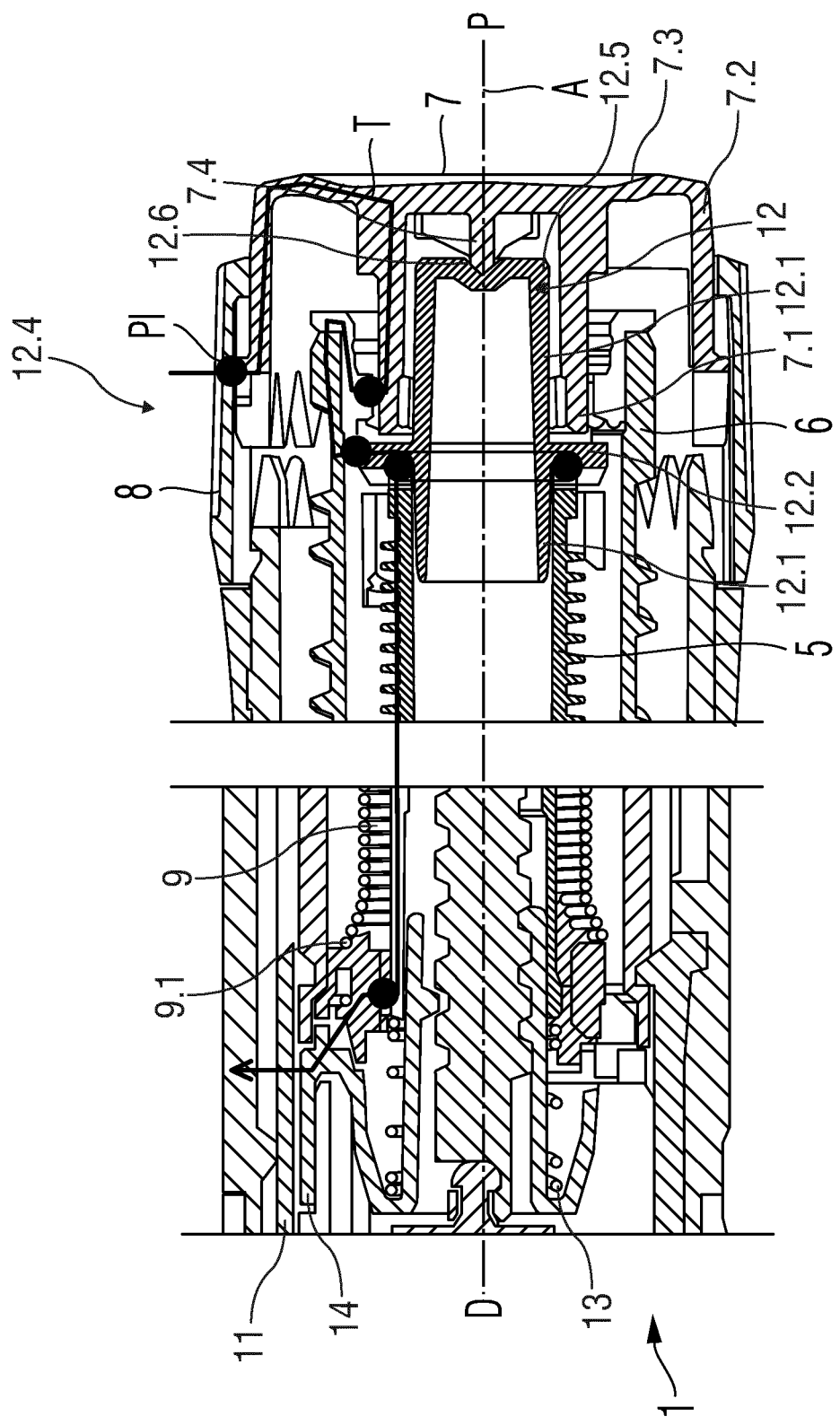
FIG. 2 is a schematic view of the drive train in the wind-up injection device of FIG. 1.

FIG. 1 shows a longitudinal section of an exemplary embodiment of a wind-up injection device 1 as known from the state of the art. FIG. 2 shows a schematic view on the drive train T for loading the drive spring 9.

For protection of a driving function during dose setting and dose dispensing, the wind-up injection device 1 comprises at least a drivable expelling mechanism 5 adapted to move a piston rod 4 in order to dispense the dose of medicament. The drivable expelling mechanism 5 may be configured as a drive sleeve or hollow drive part. In the further description, the drivable expelling mechanism 5 is further mentioned as drive sleeve 5.

The injection device 1 further comprises a drive spring 9 adapted to move the drive sleeve 5. The injection device 1 may comprise at least one restraining element not shown in detail adapted to partially fix the drive spring 9 against axial and rotational movement with respect to the at least one restraining element.

The wind-up injection device 1 may further comprise a housing 2, a cartridge holder 3, a number sleeve 6, a button 7, a dose selector 8, a cartridge 10, a gauge element 11, a clutch element 12, a clutch spring 13 and a bearing 14. A needle assembly (not shown) usually comprises a needle and a needle hub which is attachable to the cartridge 10. A needle cover may be provided as additional components.

The wind-up injection device 1 further comprises a longitudinal axis A extending from a proximal end P to a distal end D of the wind-up injection device 1. In the present application, the proximal direction refers to a direction that under use of the wind-up injection device 1 is directed away from a drug delivery site of a patient. Correspondingly, the distal direction refers to a direction that under use of the wind-up injection device 1 is directed toward the drug delivery site of the patient. A direction perpendicular to and pointing towards the longitudinal axis A is defined as a radially inward direction. A direction perpendicular to and pointing away from the longitudinal axis A is defined as a radially outward direction.

The housing 2 is configured as a substantially tubular body receiving the components of the wind-up injection device 1 mentioned above. The cartridge holder 3 is arranged on a distal end of the housing 2 and attached thereto. The cartridge holder 3 receives the cartridge 10 from which a number of doses of a medicament may be dispensed by displacing a stopper 15 distally within the cartridge 10, wherein the stopper 15 is coupled to the piston rod 4. The distal end of the cartridge holder 3 may be provided with means for attaching a needle assembly (not shown), the needle assembly comprising a needle, a needle hub and a needle cover.

The piston rod 4 is threaded to the housing 2, wherein the piston rod 4 comprises an outer thread that engages a corresponding inner thread of the housing 2. A distal end of the piston rod 4 is engaged with the bearing 14 which acts on the stopper 15. The piston rod 4 is rotationally locked to the drive sleeve 5 such that the piston rod 4 moves axially with respect to the drive sleeve 5 when rotated.

The drive sleeve 5 has a substantially hollow cylindrical shape and encloses the piston rod 4. The drive sleeve 5 is proximally engaged to the clutch element 12 and distally engaged to the clutch spring 13. The drive sleeve 5 is further arranged within the number sleeve 6 and allowed to move distally with respect to the housing 2, the piston rod 4 and the number sleeve 6 against a bias of the clutch spring 13. The drive sleeve 5 is rotationally locked to the housing 2 during a dose setting and rotationally uncoupled from the housing 2 during dispensing a dose of medicament. Furthermore, the drive sleeve 5 is rotationally locked to the number sleeve 6 during dose dispensing.

The number sleeve 6 comprises a substantially tubular shape and is marked with a sequence of numbers on an outer circumference, which are visible through the gauge element 11. The number sleeve 6 is rotationally locked to the dose selector 8 during dose setting and thus rotated during dose setting via the dose selector 8. During dose dispensing, the number sleeve 6 is rotated together with the drive sleeve 5 by the drive spring 9. The number sleeve 6 is further axially locked to the housing 2 and rotationally coupled to the button 7 during dose setting.

The button 7 forms the proximal end of the wind-up injection device 1 and is rotatably engageable to the dose selector 8 via the clutch element 12. To activate a drug delivery mechanism, the button 7 is pressed distally as it is described further below.

The button 7 is for example arranged onto the clutch element 12 on the proximal end P of the device 1. The button 7 comprises an outer button wall 7.1 coupled to the dose selector 8. The button 7 may further comprise an inner button wall 7.2 coupled to the clutch element 12. The button 7 is formed as a double-walled tube comprising a tubular outer button wall 7.1 and a tubular inner button wall 7.2 that are coaxial to each other and to the longitudinal axis A. The proximal front surface of the button 7 is closed by a button lid 7.3.

The dose selector 8 is configured as a sleeve-like component for example with a ribbed outer surface in order to provide a grippable surface. The dose selector 8 is furthermore locked against axial movement with respect to the housing 2 and locked against rotational movement with respect to the button 7. A rotation of the dose selector 8 during dose setting charges the drive spring 9 in order to energize the drug delivery mechanism.

The drive spring 9 is inserted for example into the number sleeve 6, thereby enclosing a distal portion of the drive sleeve 5. The drive spring 9 comprises a distal spring end 9.1 fixed to the housing 2 and a proximal spring end 9.2 (shown in FIG. 1) fixed to the number sleeve 6. The drive spring 9 is biased or charged during dose setting by rotating the dose selector 8 with respect to the housing 2. Because the dose selector 8 is rotationally locked to the number sleeve 6 and the number sleeve 6 is fixed to the proximal spring end of the drive spring 9, the drive spring 9 is biased and decreases its diameter approaching a torque axis as described further below.

Further components of the wind-up injection device 1 are for example the gauge element 11, the clutch element 12, the clutch spring 13 and the bearing 14.

The gauge element 11 comprises a generally plate- or band-like component having a central aperture (window) allowing viewing a portion of the number sleeve 6. The gauge element 11 is rotationally locked to the housing 2 but allowed to translate axially with respect to the housing 2.

The clutch element 12 is engaged to the number sleeve 6 and rotationally locked thereto. The clutch element 12 is further locked against rotational movement to the button 7 at least during dose setting. The clutch element 12 provides an audible and/or tactile feedback for the user during dose setting and dose dispensing. The clutch element 12 may comprise a ratchet 12.4, thereby preventing the drive spring 9 from discharging via the number sleeve 6 and the drive sleeve 5.

The clutch spring 13 may be a compression spring and defines the axial position of the drive sleeve 5, the clutch element 12 and the button 7. The clutch spring 13 applies a force on the drive sleeve 5 in a proximal direction. This spring force is reacted via the drive sleeve 5, the clutch element 12 and the button 7, and further reacted by the dose selector 8 to the housing 2.

The bearing 14 is engaged to a distal end of the piston rod 4 and acts on the stopper 15 in a distal direction. The bearing 14 is axially locked and rotationally coupled to the piston rod 4.

In order to perform a drug delivery process, the wind-up injection device 1 may be operated according to the following exemplary method.

The user selects a variable dose of medicament by rotating the dose selector 8 clockwise, which generates an identical rotation of the number sleeve 6 with respect to the housing 2. A rotation of the number sleeve 6 causes the charging of the drive spring 9 as mentioned above, thereby increasing rotational energy stored within. As the number sleeve 6 rotates, the gauge element 11 translates axially due to its threaded engagement, thereby showing the value of the dialled dose.

Thus, a drive train T for charging the torsion drive spring 9 comprises the dose selector 8, the button 7, the clutch element 12 optionally comprising the ratchet 12.4 and the number sleeve 6. As the ratchet 12.4 is supported against the housing 2 via the drive sleeve 5, the drive train T also comprises the drive sleeve 5.

As a dose is set, the user may activate the drug delivery mechanism by depressing the button 7 in the distal direction, thereby initiating dose dispensation.

As a result, the button 7 and the dose selector 8 are rotationally disconnected from the number sleeve 6 and the drive spring 9. The clutch element 12 and the drive sleeve 5 move axially together with the button 7, thereby engaging the drive sleeve 5 to the number sleeve 6 such that relative rotation between the drive sleeve 5 and number sleeve 6 is prevented. Furthermore, the engagement between the housing 2 and the drive sleeve 5 releases, thus the drive sleeve 5 is allowed to rotate and is driven by the drive spring 9 via the number sleeve 6 and the clutch element 12.

Rotation of the drive sleeve 5 causes rotation of the piston rod 4 which is axially translated due to its threaded engagement to the housing 2. Rotation of the number sleeve 6 causes the gauge element 11 to move axially back into a zero position, whereby a zero dose abutment (not shown) stops the drug delivery mechanism.

Since the bearing 14 is directionally engaged with the stopper 15, the bearing 14 does not rotate when the piston rod 4 rotates. Instead, the bearing 14 is axially translated during dose dispense.

If the user releases the button 7, the clutch spring 13 returns the drive sleeve 5 to an 'at rest' position (together with the clutch element 12 and the button 7), thereby engaging the drive sleeve 5 with the housing 2, preventing further rotation and stopping dose dispense. The user may then rotate the dose selector 8, so that the number sleeve 6 returns to the zero dose abutment.

The drive train T for the wind-up injection device 1 for injecting a liquid drug comprises for example at least the torsional energy storage 9 (also referred to as drive spring 9) adapted to be loaded or unloaded by the rotatable element 6 (also referred to as number sleeve 6), the rotatable user handle 8 (also referred to as dose selector 8) coupled with the button 7, the rotationally drivable expelling mechanism 5, e.g. the drive sleeve, adapted to expel the liquid drug and the clutch element 12 coupled with the torsional energy storage 9 via the rotatable element 6 and comprising a ratchet 12.4 for maintaining the rotatable element 6 at one of a number of discrete angular positions against the torque of the torsional energy storage 9, wherein the clutch element 12 is adapted to transmit a torque from the user handle 8 via the rotatable element 6 to the torsional energy storage 9 or alternatively from the rotatable element 6 to the expelling mechanism 5, and wherein the ratchet 12.4 is switchable from one position to an adjacent position by a torque transmitted from the user handle 8 to the torsional energy storage 9, and wherein the drive train T is adapted to dampen torque peaks by a flexible impact portion 17 (shown in different embodiments in the following FIGS. 4 to 17) in the area of the clutch element 12.

When setting a dose, a torque is transferred from the dose selector 8 via the button 7, the number sleeve 6 onto the proximal spring end 9.2 of the drive spring 9. With the button 7 being released, i.e. in "rest" position, the ratchet 12.4 engages the drive sleeve 5 that is rotationally locked to the housing 2 such that the number sleeve 6 is held in one of a predetermined number of angular positions, thereby preventing an unloading of the drive spring 9. Along the drive train T, form-fitting or positive interfaces PI transfer the torque from the dose selector 8 onto the button 7, from the button 7 onto the number sleeve 6 and from the number sleeve 6 onto the clutch element 12.

Any of these positive interfaces PI inevitably provides a rotational play. Furthermore, due to the distance the torque is transmitted along the longitudinal axis A, torsionally weak elements such as the drive sleeve 5 may twist under torque. Besides preventing unloading of the drive spring 9, the ratchet 12.4 causes a discontinuous turning resistance when dialing a dose via the dose selector 8. Thereby, a peak torque required to step the ratchet 12.4 into the next angular position is immediately followed by a low torque. These torque discontinuities that are countered by the torque accumulated both in the drive spring 9 and in the twisted torsionally weak elements may result in an end-to-end stressing of the total rotational play over all positive interfaces PI that appears as rattling along the drive train T.

Figure 3:
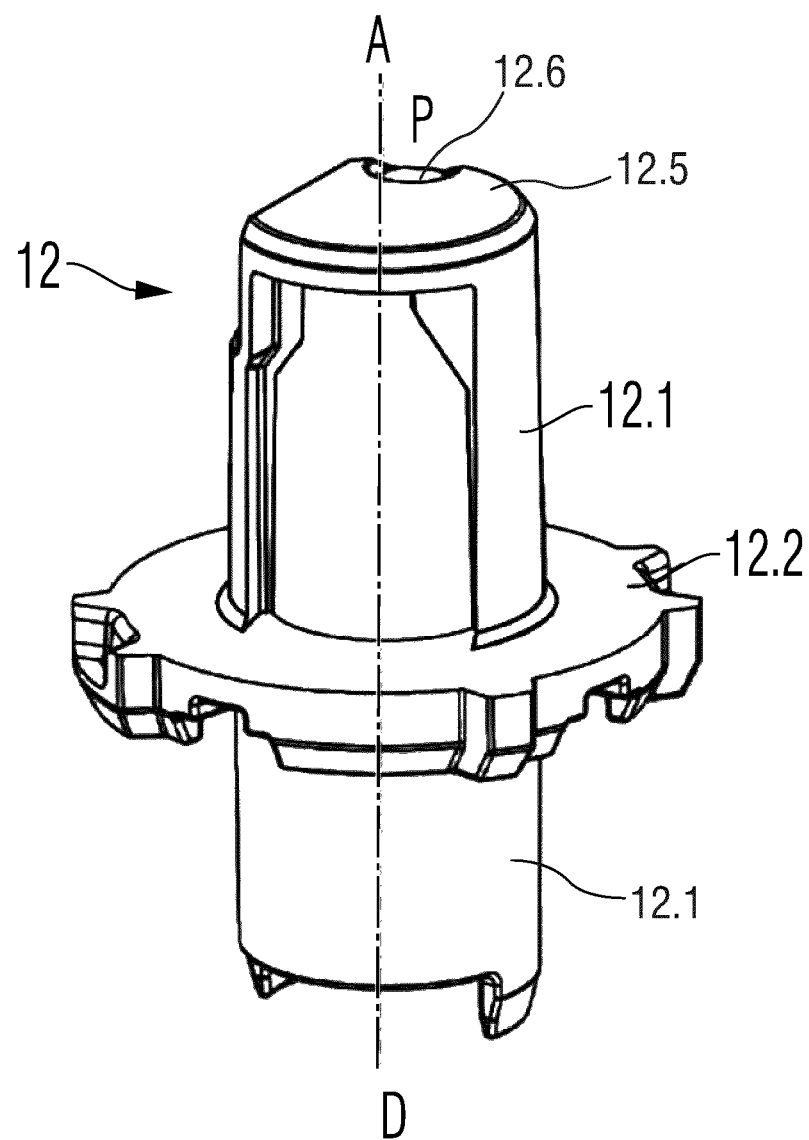
FIG. 3 is a perspective view of an exemplary embodiment of a clutch element of the wind-up injection of FIG. 1, FIGS. 4 and 5 show schematic views of an exemplary embodiment of a flexible impact portion for a clutch element of a wind-up injection device.

FIG. 3 shows a perspective view of an exemplary embodiment of a clutch element 12 in more detail.

The clutch element 12 comprises a substantially hollow cylindrical clutch section 12.1 a clutch plate 12.2. The clutch section 12.1 extends axially between a proximal end P and a distal end D. A distal portion of the cylindrical clutch section 12.1 extends between the distal end of the cylindrical clutch section 12.1 and the clutch plate 12.2. A proximal portion of the cylindrical clutch section 12.1 extends between the clutch plate 12.2 and the proximal end of the cylindrical clutch section 12.1.

On the proximal end of the clutch element 12, a clutch lid 12.5 is formed closing the cylindrical clutch section 12.1. The outer or proximal surface of the clutch lid 12.5 provides a blind hole 12.6. The blind hole 12.6 is arranged centrically and is formed such that it receives a guide pin 7.4 that centrically protrudes from the button lid 7.3 in the distal direction. The clutch element 12 is forced by the clutch spring 13 in the proximal direction towards the inner or distal surface of the button lid 7.3, such that the guide pin 7.4 engages the blind hole 12.6. By their concentric arrangement, the guide pin 7.4 and the blind hole 12.6 form a trigger button bearing 18 that hold the trigger button 7 coaxially with the longitudinal axis A and with respect to the clutch element 12.

The distal end of the cylindrical clutch section 12.1 is arranged inside the proximal end of the drive sleeve 5. The proximal end of the cylindrical clutch section 12.1 is arranged inside the distal end of the button 7. The clutch element 12 and the drive sleeve 5 are arranged concentrically relative to each other and with respect to the longitudinal axis A. The clutch element 12 and the button 7 are arranged concentrically relative to each other and with respect to the longitudinal axis A.

When setting the dose via the dose selector 8, the drive sleeve 5 is rotationally locked to the housing 2 while the clutch element 12 is rotationally locked to the number sleeve 6 that is rotated to load the drive spring 9.

Figure 4:
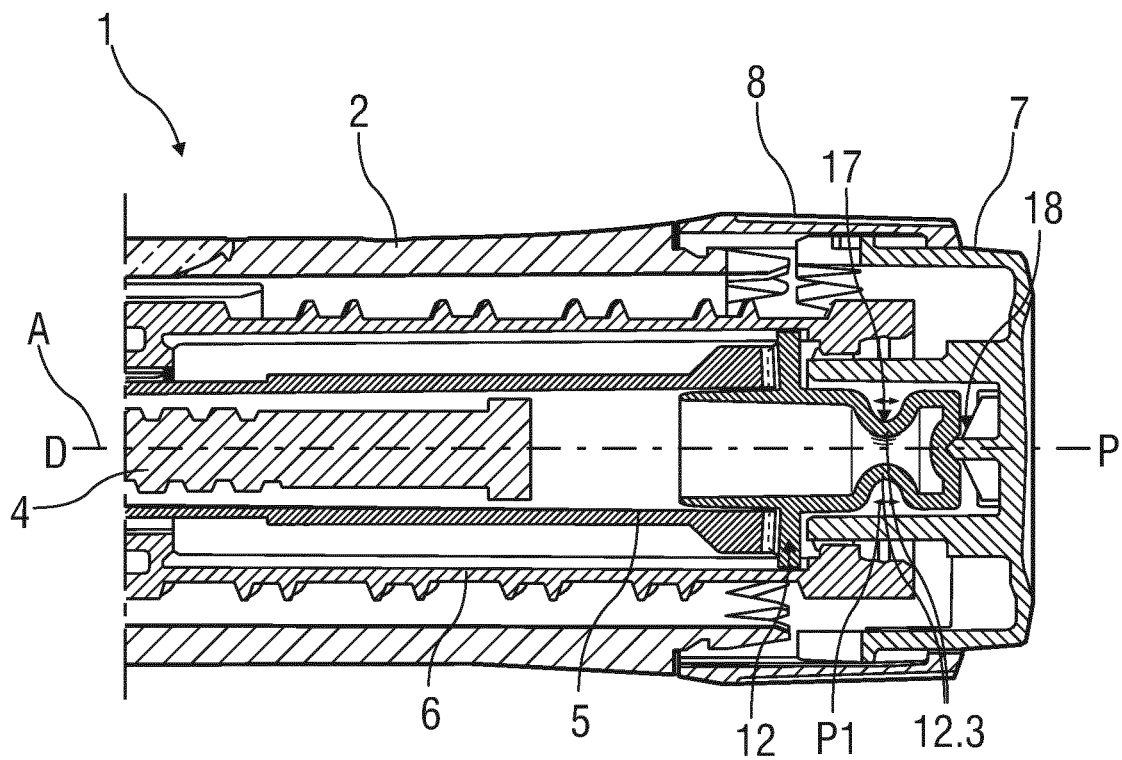
Figure 5:
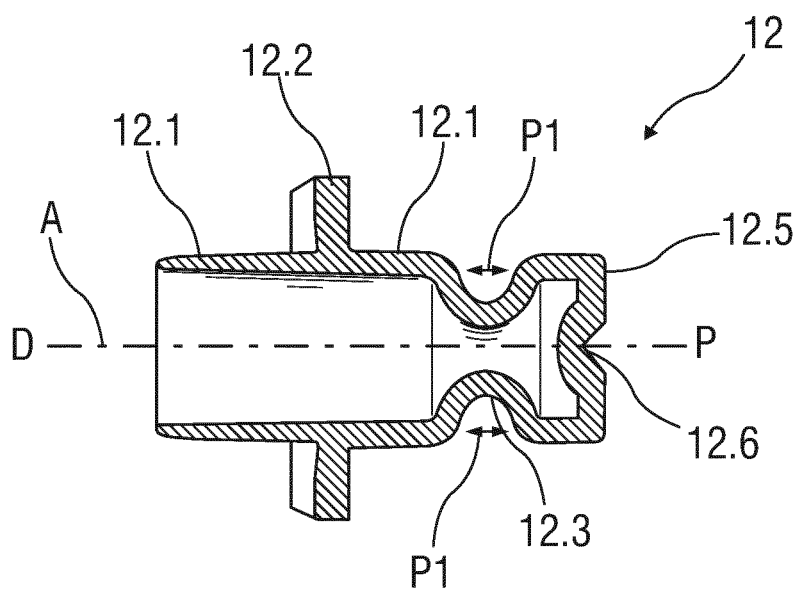

FIGS. 4 and 5 show an embodiment of a flexible impact portion 17 for damping axial impacts, e.g. torque peaks, in the drive sleeve 5.

FIG. 4 shows a schematic longitudinal section of a driving mechanism located at the proximal end P of a wind-up injection device 1 according to an embodiment with a modified clutch element 12, which is shown in more detail in FIG. 5. Along the cylindrical clutch section 12.1, a flexible impact portion 17 may be formed as a compressible portion arranged in an area of the axial clutch bearing 18, in particular adjacent the clutch bearing 18 between the clutch element 12 and the button 7. For example the compressible portion is formed into the proximal cylindrical clutch portion 12.1.

The flexible impact portion 17 may be configured as a recess 12.3 inserted into the proximal cylindrical clutch portion 12.1. The flexible impact portion 17 may be also configured as a radial denting which is formed that radially inwards dents the cylindrical clutch section 12.1, thereby providing the clutch element 12 an axial resilience along the longitudinal axis A. By this axial resilience, the clutch element 12 is axially resiliently pressed towards the guide pin 7.4 of the button 7, such that the rotational frictional resistance caused by the clutch bearing 18 formed of the guide pin 7.4 and the blind hole 12.6 is increased and continuous within the axial tolerance of the clutch element 12 relative to the button 7. In other words: On the outside surface of the proximal end of the cylindrical clutch section 12.1, at least one circumferential recess 12.3 is formed.

Said axial resilience of the clutch element 12 is dampened by the flexible impact portion 17 according to the arrow P1 to avoid rattle noises that are caused by soft torsion elements and by positive-locking interfaces along the drive train T for charging or discharging the torsion drive spring 9. In particular, by such an increased friction due to the recess 12.3, torque peaks along the drive train T are reduced. With other words: The flexible impact portion 17 increases the frictional resistance that the user must overcome to turn the dose selector 8 and press the button 7. Thereby, the torque peaks along the drive train T are reduced or dampened.

As a further advantage, the axial play between the drive sleeve 5 and the clutch element 12 and/or the clutch element 12 and the button 7 are/is reduced, thereby reducing unwanted rattling and tactile discontinuities that otherwise may incur upon rotation of the clutch element 12 such that the user experiences a smoothened and softer operation of the wind-up injection device 1.

The clutch element 12 is urged by the clutch spring 13 via the drive sleeve 5 axially towards the inner or distal face of the button lid 7.3, such that the recess 12.3 or fold frictionally engages the proximal face of the clutch lid 12.5, thereby causing frictional resistance against a rotation of the clutch element 12 relative to the button 7.

The width of the recess 12.3 along the longitudinal axis is chosen such that the recess 12.3 is compressed when the distal tip of the guide pin 7.4 is fully received in the blind hole 12.6 of the clutch element 12. Said increased frictional axial and rotational resistance adds to the torque required to turn the dose selector 8 against the drive spring 9 and the ratchet 12.4 such that the relative difference between torque peaks and torque minima caused by the ratchet 12.4 is reduced or dampened. Thus, also rattle noises that are caused by soft torsion elements and by positive-locking interfaces along the drive train T for charging or discharging the torsion drive spring 9 are dampened.

Figure 6:
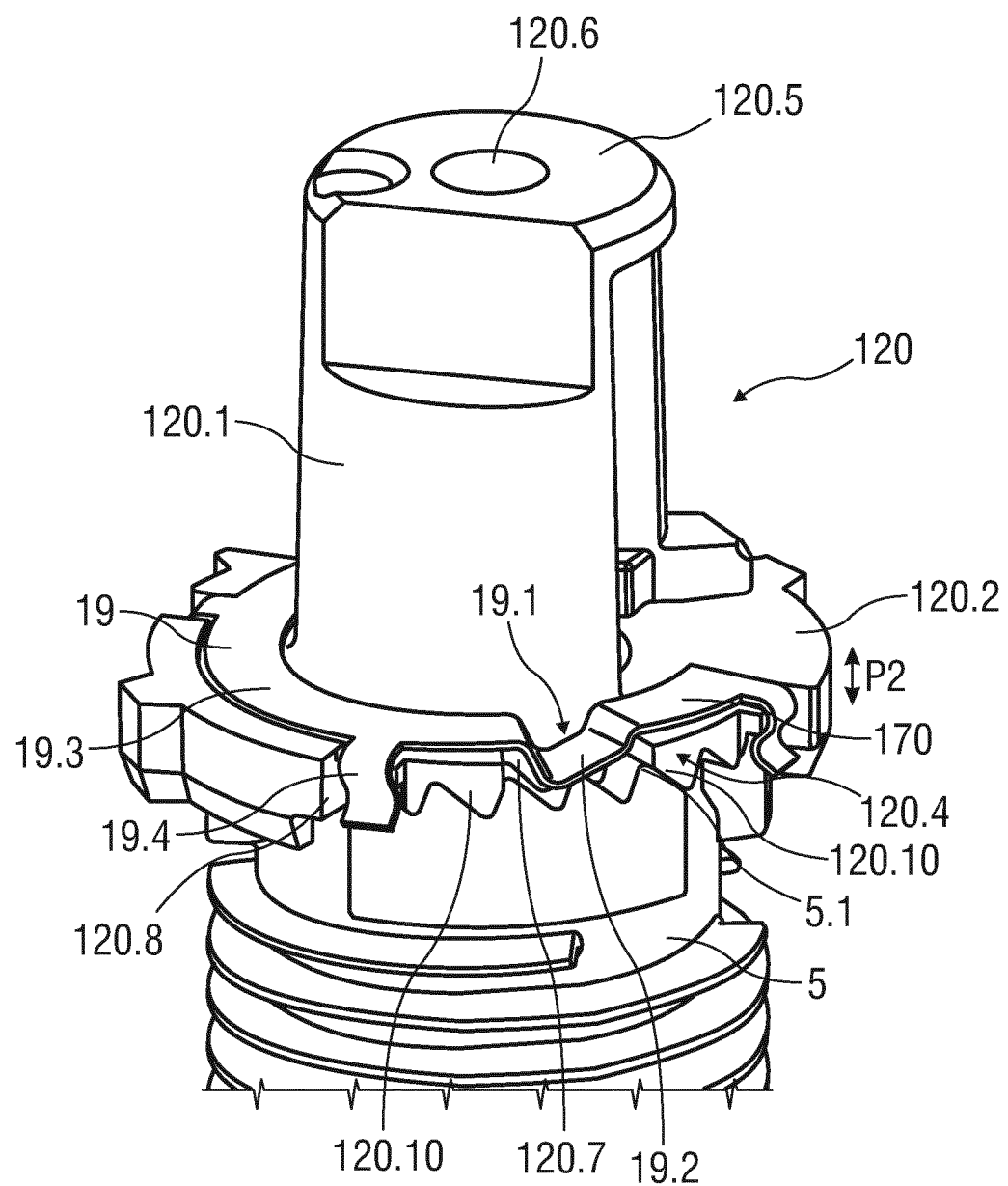
FIGS. 6 to 8 show schematic views of a further exemplary embodiment of a flexible impact portion for a clutch element of a wind-up injection device.
Figure 7:
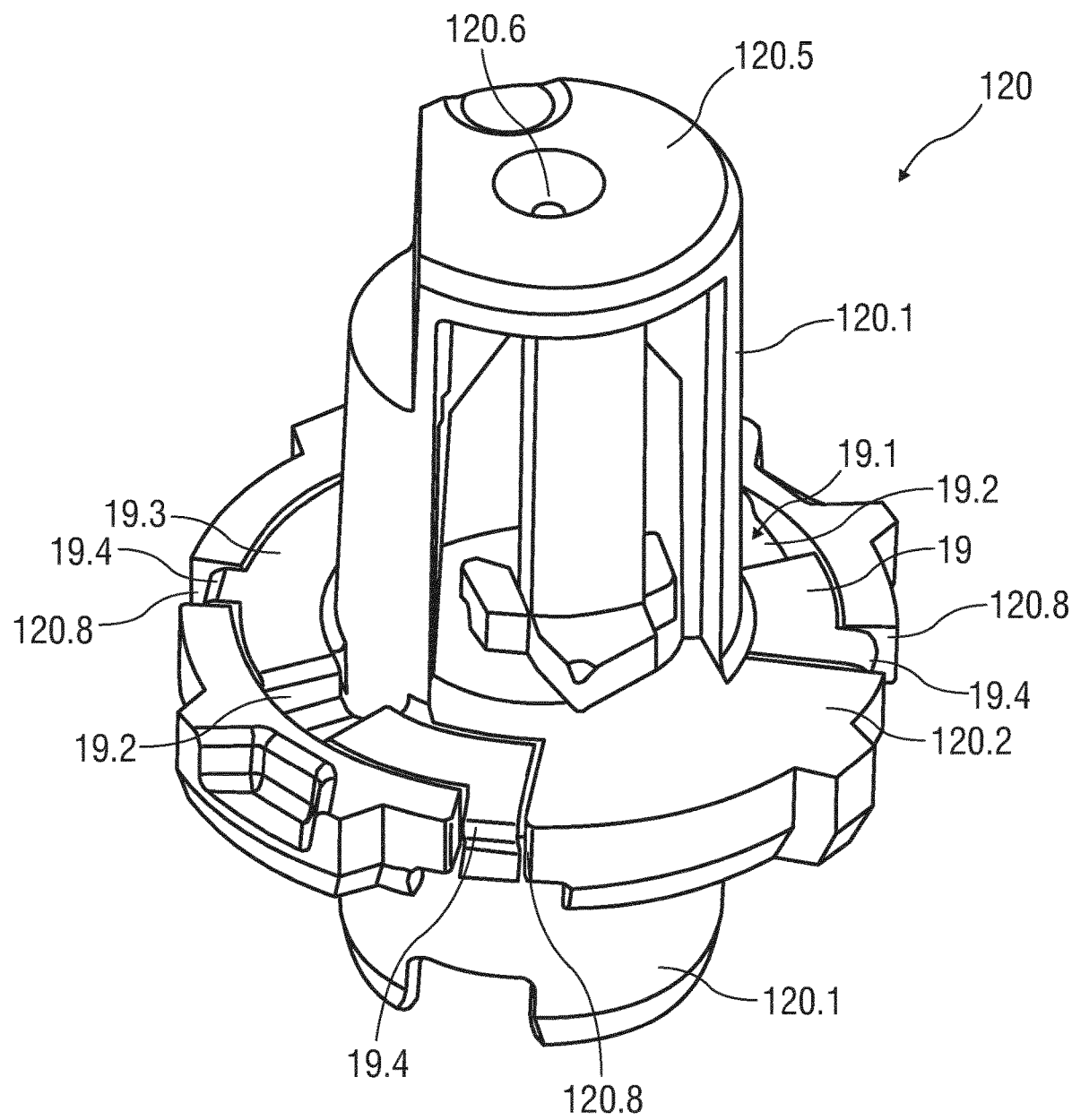
Figure 8:
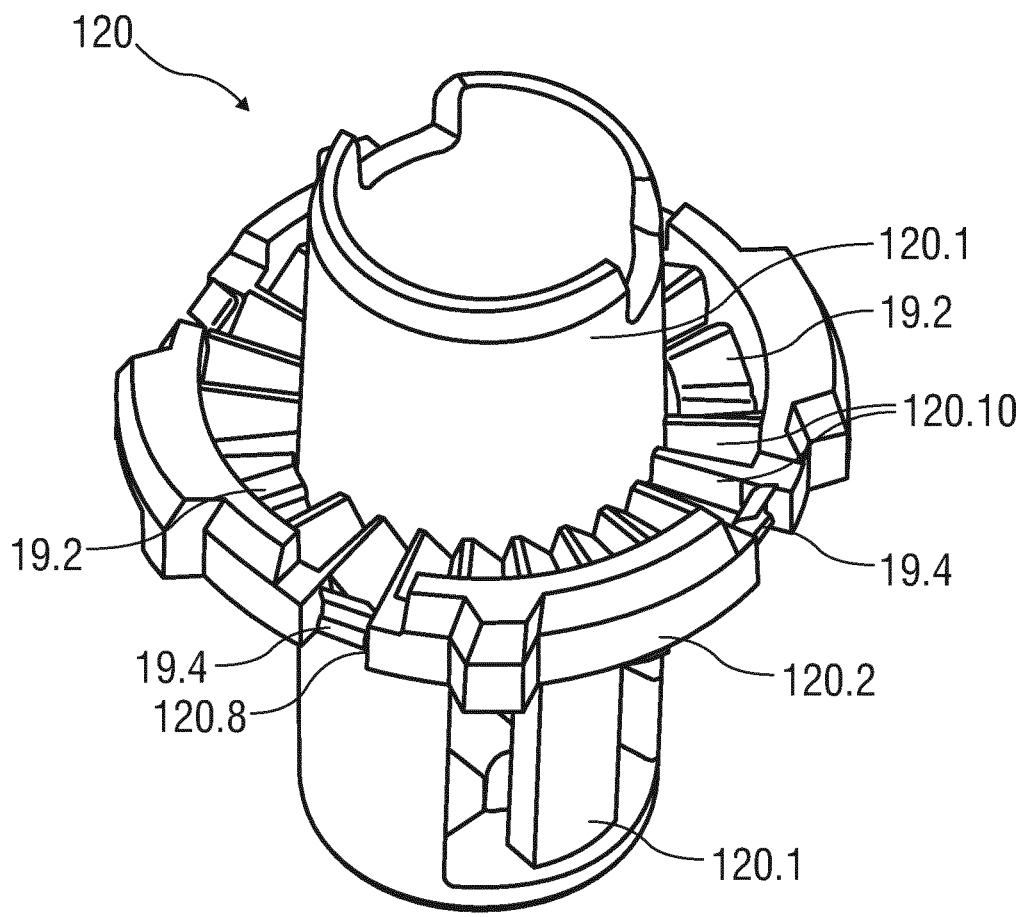

FIGS. 6 to 8 show schematic views of a further exemplary embodiment of a flexible impact portion 170 for a clutch element 120 of the wind-up injection device 1.

The flexible impact portion 170 is configured as at least a flexible metal element 19, e.g. a spring element. The flexible metal element 19 is configured to apply a spring force when the clutch element 120 contacts the drive sleeve 5.

The flexible metal element 19 is arranged in the area of the ratchet 120.4. In particular, the flexible metal element 19 is partially arranged between the clutch element 120 and the drive sleeve 5.

For example, the flexible metal element 19 is formed at least partially as a spring element 19.1 having a flexible ramp profile 19.2. The flexible ramp profile 19.2 acts axially and/or tangentially between the clutch element 120 and the drive sleeve 5. The flexible metal element 19 is arranged onto the clutch plate 120.2, in particular on the upper surface. The spring element 19.1 protrudes from a basis 19.3 of the flexible metal element 19 through an opening 120.7 towards the drive sleeve 5, in particular towards teeth 5.1 of the drive sleeve 5. The spring element 19.1 with its flexible ramp profile 19.2 damps axial forces of the ratchet 120.4 during dialing process, in particular in a correction direction.

In particular, the flexible ramp profile 19.2 is configured, in particular angled or ramped, to slow the contact speed in a correction direction. For example, the contact between the flexible metal element 19, e.g. the top of the flexible ramp profile 19.2, and the drive sleeve 5, e.g. the top of its teeth 5.1, occurs midway through the engagement of the clutch teeth 120.10 and the drive sleeve teeth 5.1 with each other. In dose dialing or selecting direction, the flexible ramp profile 19.2 does not resist tangential motion.

The axial resilience of the clutch element 120 with respect to the drive sleeve is dampened by the flexible metal element 19, in particular by its flexible ramp profile 19.2, according to the arrow P2 to avoid rattle noises that are caused by soft torsion elements and by positive-locking interfaces along the drive train T for charging or discharging the torsion drive spring 9.

In particular, drive sleeve teeth 5.1 initially contacts the flexible ramp profile 19.2 when the clutch element 120 and the drive sleeve 5 engage each other. Due to an increased friction provided by the flexible ramp profile 19.2, torque peaks along the drive train T are reduced. With other words: The flexible metal element 19 increases the frictional resistance that the user must overcome to turn the dose selector 8 and press the button 7. Thereby, the torque peaks along the drive train T are reduced or dampened.

The flexible metal element 19 comprises further at least one clamping protrusion 19.4 to hold the flexible metal element 19 on the clutch element 120. The clamping protrusion 19.4 may be configured as a clamping arm or hook. The clutch plate 120.2 comprises a corresponding retaining slot 120.8 or flange.

In a possible embodiment, the flexible metal element 19 may comprise a few number of flexible ramp profiles 19.2 and/or a few number of clamping protrusions 19.4.

In particular, the clutch plate 120.2 comprises along its outside extent or circumference clutch teeth 120.10 for engaging with the corresponding drive sleeve teeth 5.1, one or more retaining slots 120.8 for retaining one or more clamping protrusions 19.4 and one or more openings 120.7 for the arranging one or more corresponding flexible ramp profiles 19.2.

According to the disclosure, the flexible metal element 19 is formed as a spring having at least two protruding spring ramp elements as flexible ramp profiles 19.2. The two protruding spring ramp elements are arranged opposite each other.

In particular, the flexible metal element 19 may also be formed as a washer or a partially collared disc. The flexible ramp profile 19.2 as well as the clamping protrusion 19.4 extends from the clutch plate 120.2 in the same direction towards the drive sleeve 5.

FIG. 7 shows the flexible metal element 19 and the clutch element 120 in an assembled state in which the flexible metal element 19 is clamped onto the clutch plate 120.2 by engaging of the clamp protrusions 19.4 within the retaining slots 120.8.

FIG. 8 shows the clutch element 120 from the ratchet side. The flexible ramp profile 19.2 protrudes through the opening 120.7 of the clutch plate 120.2.

Figure 9:
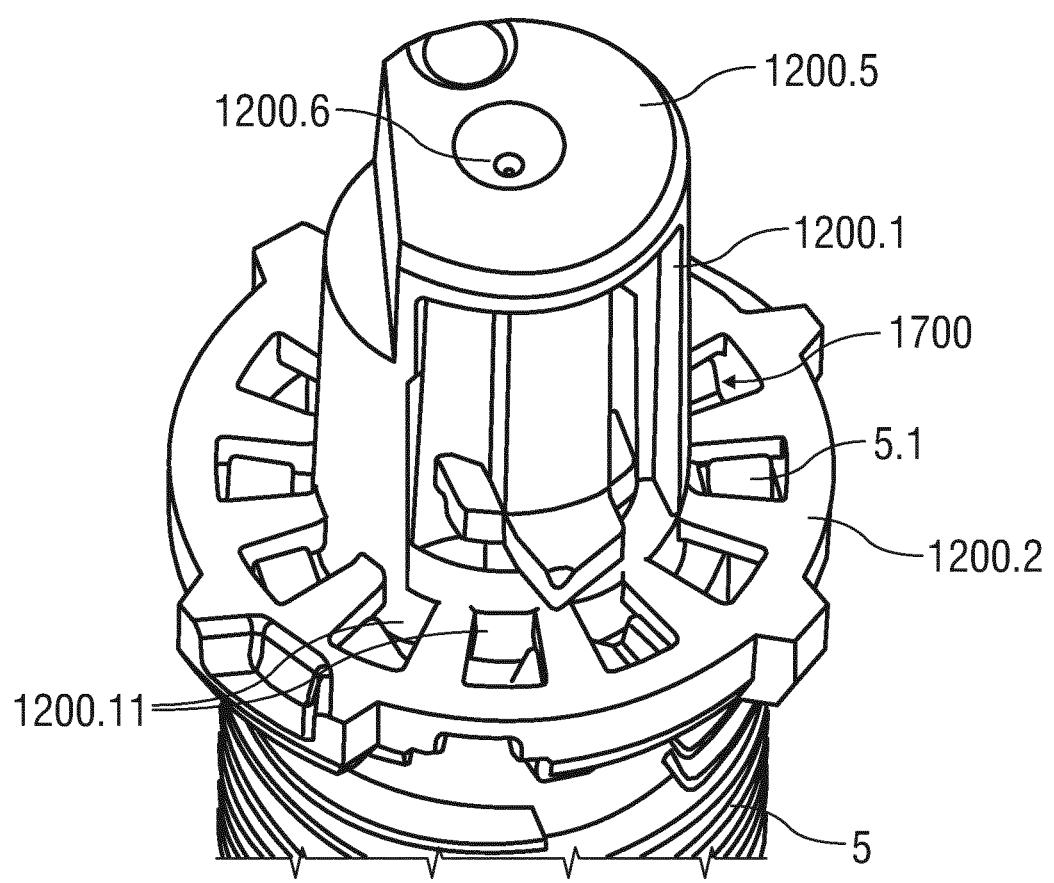
FIGS. 9 to 10 show schematic views of another exemplary embodiment of a flexible impact portion for a clutch element of a wind-up injection device.
Figure 10:
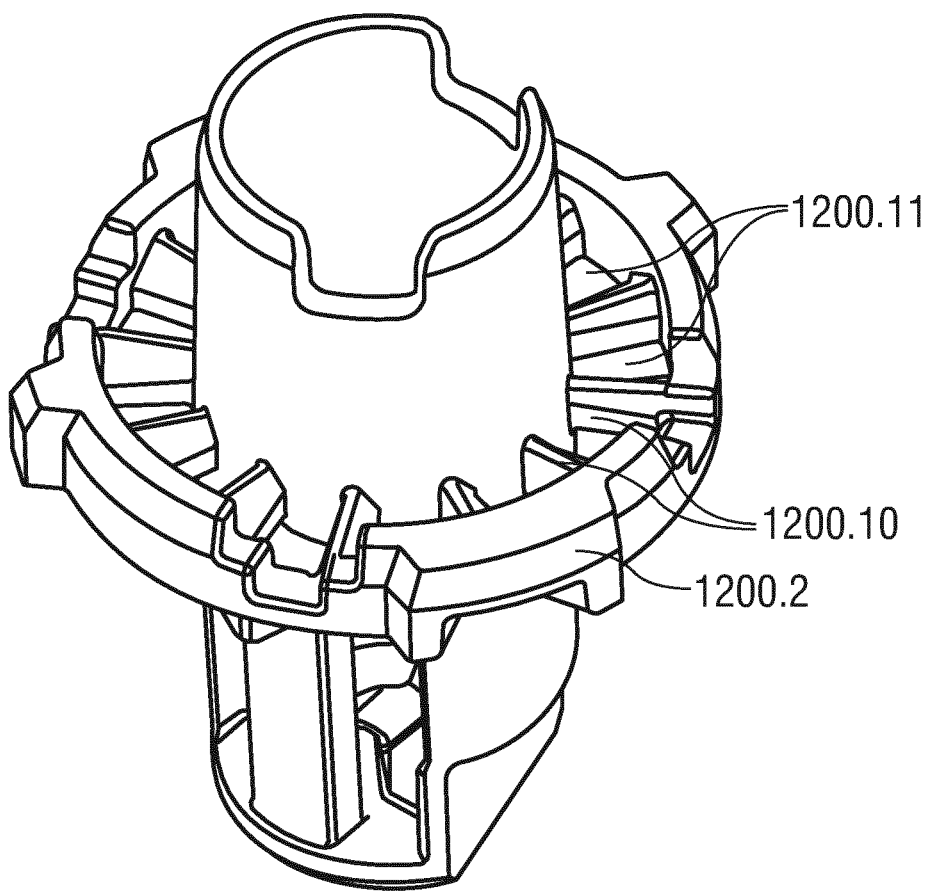

FIGS. 9 to 10 show a schematic of another exemplary embodiment of a flexible impact portion 1700 for the clutch element 1200 of the wind-up injection device 1.

The axial clutch impact currently occurs between stiff components, namely the clutch element 1200 and the drive sleeve 5.

The flexible impact portion 1700 of the clutch element 1200 is formed by a number of apertures 1200.11 arranged in the clutch plate 1200.2. Due to the apertures 1200.11 the clutch teeth 1200.10 are able to flex slightly to absorb forces.

The surface of the clutch plate 1200.2 is formed towards the proximal direction plane and flat (shown in FIG. 9). On the opposite surface of the clutch plate 1200.2 towards the distal direction, the clutch plate 1200.2 comprises the clutch teeth 1200.10 (shown in FIG. 10). In comparison with the previously described embodiments, a few number of clutch teeth 1200.10 are removed to leave the apertures 1200.11. As the drive sleeve 5 impacts the clutch plate 1200.2 during a dialing process the clutch teeth 1200.10 are configured to be able to flex slightly to absorb torque peaks and energy.

Figure 11:
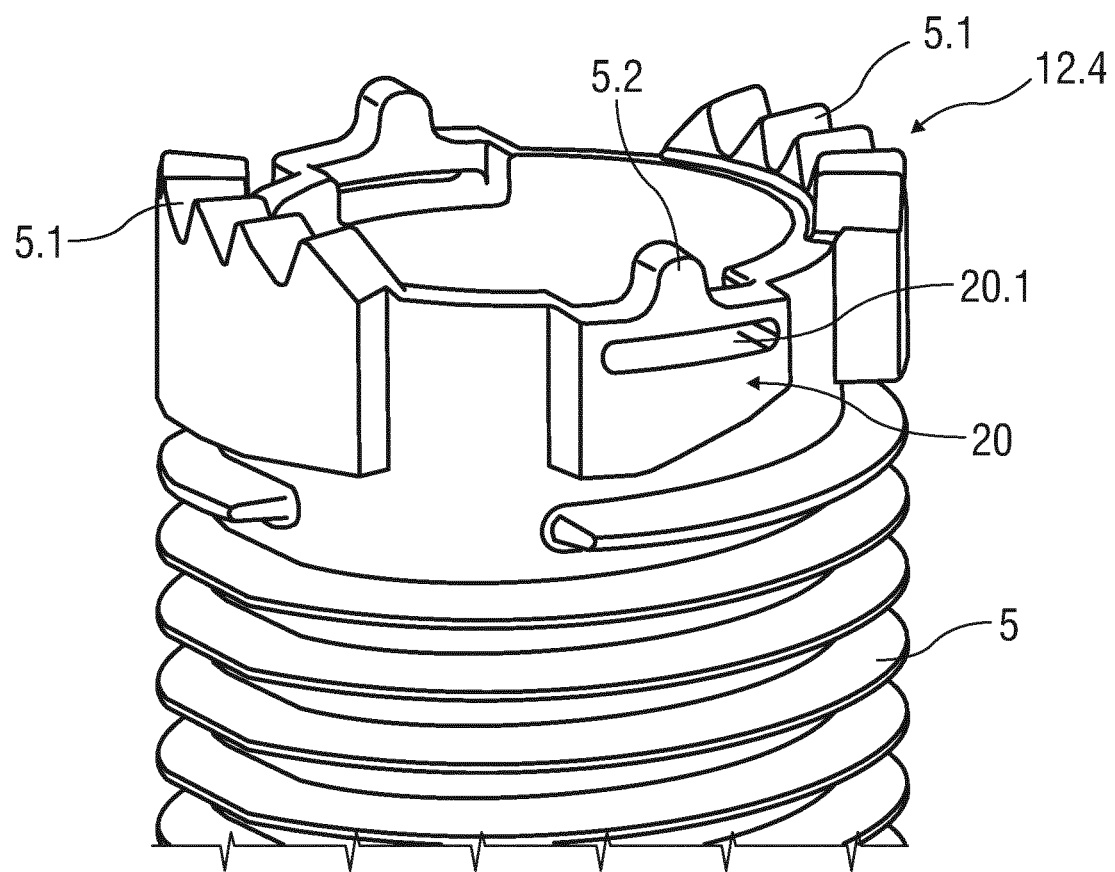
FIGS. 11 to 12 show schematic views of a further exemplary embodiment of a flexible impact portion for a clutch element of a wind-up injection device.
Figure 12:
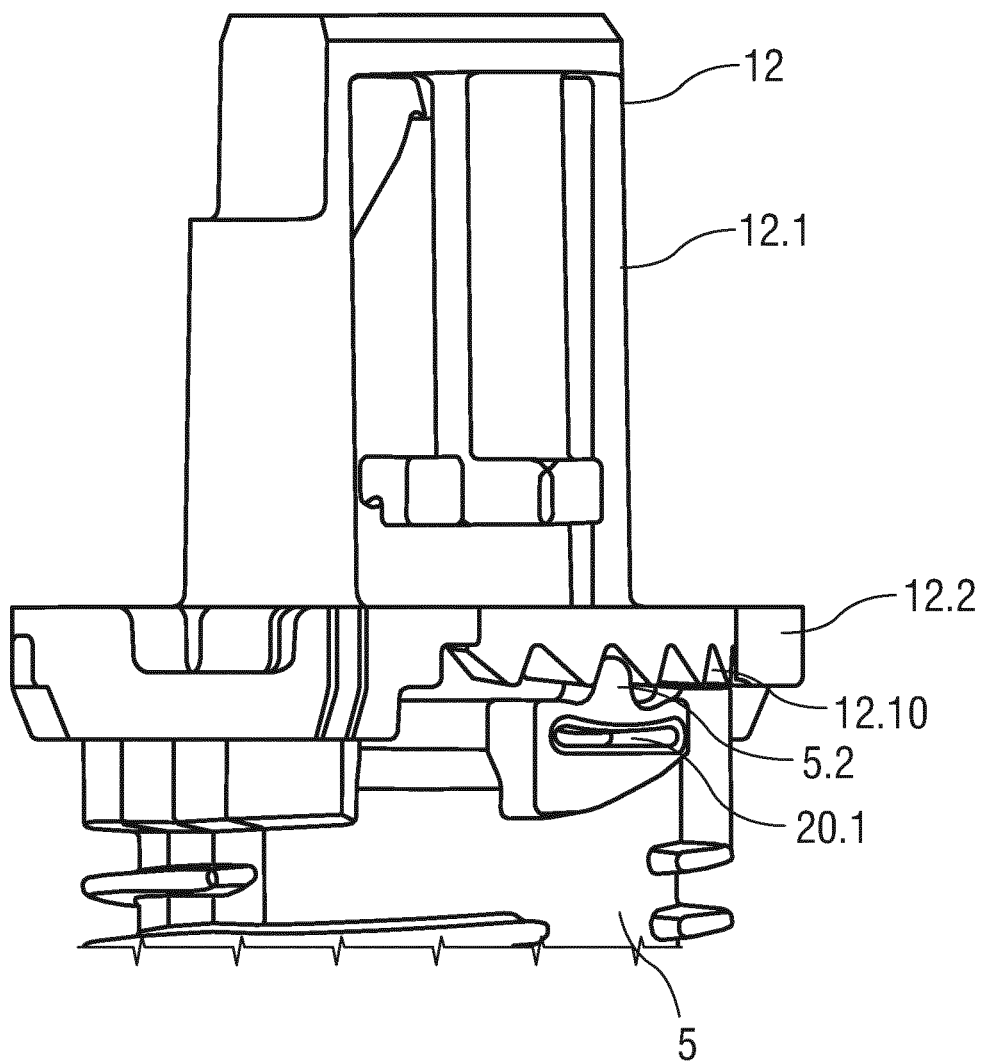

FIGS. 11 to 12 show a schematic of a further exemplary embodiment of a flexible impact portion 20 for the clutch element 12 of the wind-up injection device 1.

The flexible impact portion 20 is configured as at least a compressible portion of the drive sleeve 5. The compressible portion is arranged in the area of the ratchet 12.4, in particular between the clutch element 12 and the drive sleeve 5. For example, the compressible portion is configured as a slot 20.1 in an edge region of the drive sleeve 5.

The slot 20.1 is arranged beneath a protruding drive sleeve tooth 5.2 of the drivable expelling mechanism. Slot 20.1 is inserted in an upper edge region which, in assembled state, arranged beneath the clutch teeth 12.10 of the clutch element 12.

The slot 20.1 is configured so that due to impact onto the drive sleeve 5 the drive sleeve tooth 5.2 deflects.

As the drive sleeve 5 impacts the clutch plate 12.2 during a dialing process the drive sleeve tooth 5.2 contacts the clutch plates 12.2, in particular clutch teeth 12.10, and flexes slightly and axially towards the distal end to absorb torque peaks and energy due to the slot 20.1 beneath the drive sleeve tooth 5.2 (shown in FIG. 12).

Figure 13:
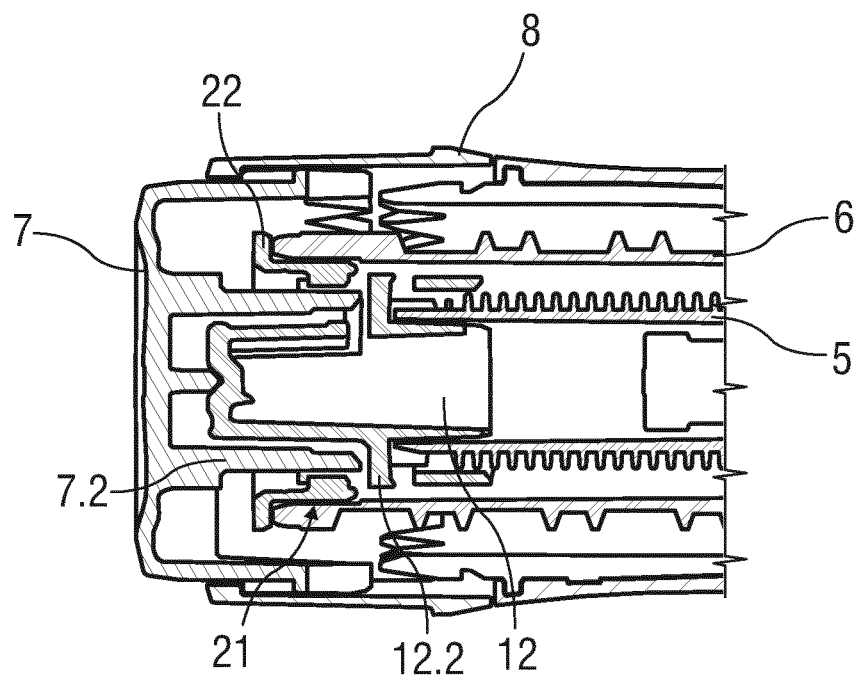
FIGS. 13 to 17 show schematic views of further exemplary embodiments of a flexible impact portion for a clutch element of a wind-up injection device.
Figure 14:
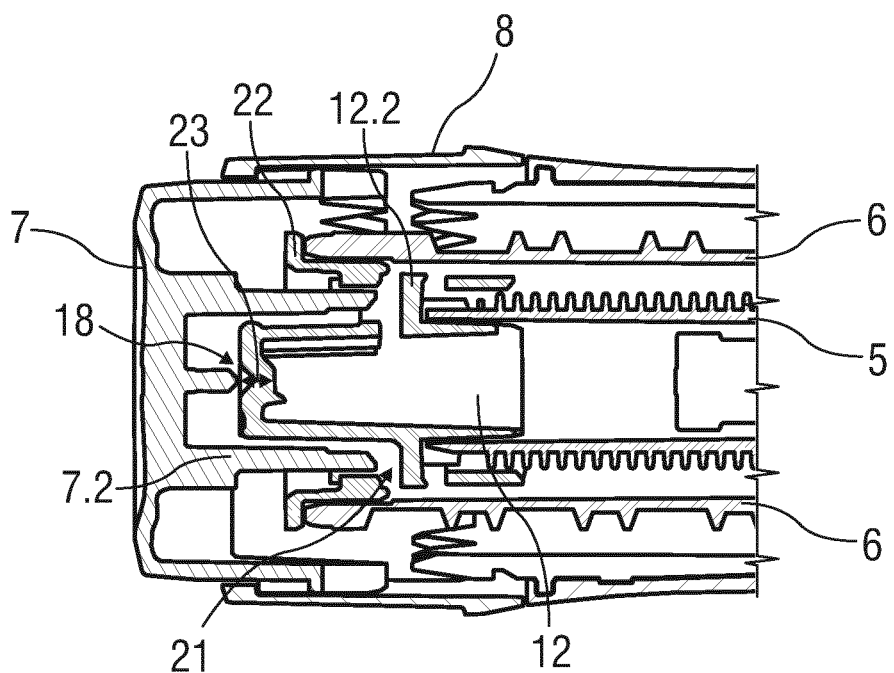
Figure 15:
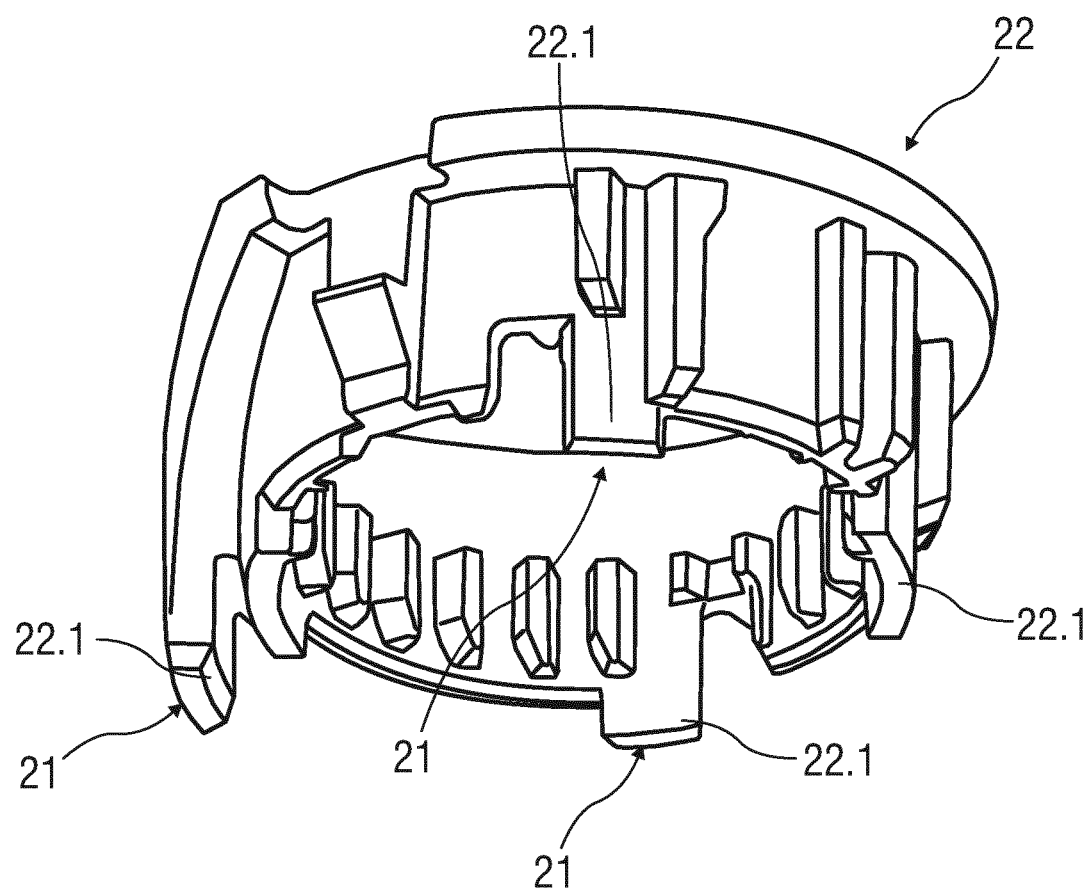

FIGS. 13 to 15 show a schematic of a further exemplary embodiment of a flexible impact portion 21 for the clutch element 12 of the wind-up injection device 1. The flexible impact portion 21 is configured as an upper number sleeve part 22. The upper number sleeve part 22 is coaxially arranged with the number sleeve 6, the clutch element 12 and the button 7.

In particular, the upper number sleeve part 22 is arranged between the proximal end of the number sleeve 6 and the distal end of the inner button wall 7.2.

In case of a longer button 7, a clearance or gap 23 is provided between the button 7 and the clutch element 12 in a dialing state, e.g. during dialing process.

In an assembled state, arms 22.1 extended from the distal end of the upper number sleeve part 22 towards the distal end of the device 1 engage the clutch element 12, in particular the clutch plate 12.2. The arms 22.1 may be configured in a flexible or compressible manner.

In case of the longer button 7, the axial load path during dialing is modified so that the clutch element 12, in particular the clutch plate 12.2, contacts the upper number sleeve part 22 rather than the button 7. The axial impact forces causing from dialing events are therefore transmitted into the upper number sleeve part 22 and the number sleeve 6. The upper number sleeve part 22 and the number sleeve 6 are stiffer than the clutch element 12.

For axial contact between the clutch element 12, in particular the clutch plate 12.2, and the upper number sleeve part 22, the upper number sleeve part 22 comprises arms 22.1 or noses protruded from the upper number sleeve part 22 towards the clutch element 12. Additionally or alternatively, the clutch plate 12.2 may comprise protrusions protruded from the clutch plate 12.2 towards the upper number sleeve part 22.

Due to the flexible arms 22.1 either on the upper number sleeve part 22 or clutch plate 12.2, the axial load path during dialing is modified so that the clutch element 12, in particular the clutch plate 12.2, contacts the flexible arms 22.1 and, thus the upper number sleeve part 22, rather than the button 7 or otherwise. The axial impact forces causing from dialing events are therefore transmitted into the upper number sleeve part 22 and the number sleeve 6. The upper number sleeve part 22 and the number sleeve 6 are stiffer than the clutch element 12.

Figure 16:
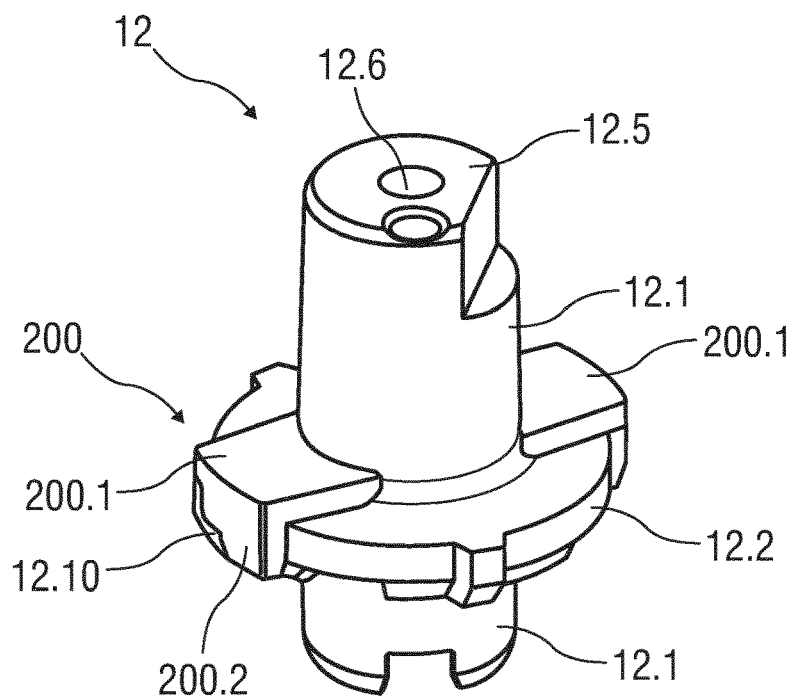
Figure 17:
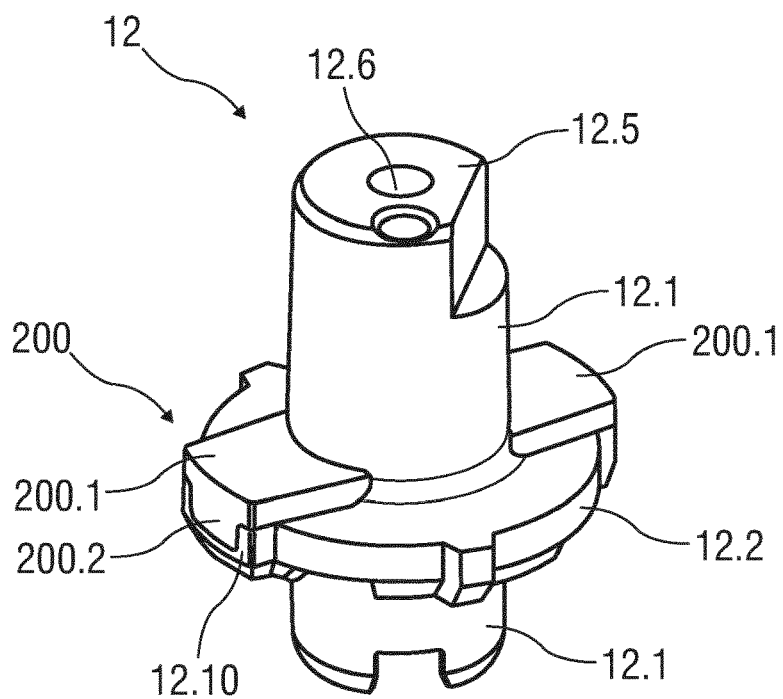

FIGS. 16 to 17 show schematic views of a further exemplary embodiment of a flexible impact portion 200 for the clutch element 12 of the wind-up injection device 1.

The flexible impact portion 200 is formed as a compressible pad 200.1 arranged onto the clutch plate 12.2 of the clutch element 12. The compressible pad 200.1 may be clipped onto the clutch plate 12.2.

The clutch plate 12.2 comprises retaining slots 12.10 in which corresponding holding elements 200.2 of the compressible pad 200.1 are engaged in a form-fitting connection, e.g. form-locked connection, or force-fitting connection, e.g. frictional connection.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body. The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')₂ fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present disclosure, which encompass such modifications and any and all equivalents thereof.

LIST OF REFERENCES 1 wind-up injection device
2 housing
3 cartridge holder
4 piston rod
5 drive sleeve
5.1 drive sleeve teeth
5.2 drive sleeve tooth
6 number sleeve, rotatable element
7 button
7.1 outer button wall
7.2 inner button wall
7.3 button lid
7.4 guide pin
8 dose selector, user handle
9 drive spring
9.1 distal spring end
9.2 proximal spring end
10 cartridge
11 gauge element
12, 120, 1200 clutch element
12.1, 120.1, 1200.1 cylindrical clutch section
12.2, 120.2, 1200.2 clutch plate
12.3 recess
12.4, 120.4, 1200.4 ratchet
12.5 clutch lid
12.6 blind hole
120.7 opening
120.8 retaining slot
12.10, 120.10, 1200.10 clutch teeth
13 clutch spring, spring
14 bearing
15 stopper
17, 170, 1700, 20, 21, 200 flexible impact portion
18 clutch bearing
19 flexible metal element
19.1 spring element
19.2 flexible ramp profile
19.3 basis
19.4 clamping protrusion
22 number sleeve part
22.1 flexible arms
23 gap
200.1 compressible pad
200.2 holding element
A longitudinal axis
P proximal end
D distal end
T drive train
PI positive interface
P1, P2 arrow

The invention claimed is:

1. A drive train for a wind-up injection device for injecting a liquid drug, comprising:
 a rotatable element,
 a torsional spring adapted to be loaded or unloaded by the rotatable element,
 a rotatable user handle coupled with a button,
 a rotationally drivable expelling mechanism adapted to expel the liquid drug, and
 a clutch element configured to couple to the rotatable element and comprising a ratchet for maintaining the rotatable element at one of a number of discrete angular positions against the torque of the torsional spring, wherein the clutch element is adapted to transmit a torque from the user handle via the rotatable element to the torsional spring or from the torsional spring via the rotatable element to the expelling mechanism, and wherein the ratchet is switchable from one position to an adjacent position by a torque transmitted from the user handle to the torsional spring, and wherein the drive train is adapted to dampen torque peaks by a flexible impact portion associated with the clutch element, thereby allowing softening of a possible impact between the clutch element and the expelling mechanism.

2. The drive train according to claim 1, wherein the clutch element comprises a cylindrical clutch section and a clutch plate which radially protrudes outwards from the cylindrical clutch section.

3. The drive train according to claim 2, wherein the flexible impact portion is formed as a compressible portion arranged adjacent an axial clutch bearing between the clutch element and the button.

4. The drive train according to claim 2, wherein the flexible impact portion is formed as a compressible portion formed in the cylindrical clutch section of the clutch element.

5. The drive train according to claim 1, wherein the flexible impact portion is configured as at least one recess in the cylindrical clutch section.

6. The drive train according to claim 1, wherein the flexible impact portion is configured as at least one flexible metal element arranged adjacent the ratchet.

7. The drive train according to claim 6, wherein the at least one flexible metal element is arranged between the clutch element and the drivable expelling mechanism.

8. The drive train according to claim 6, wherein the at least one flexible metal element is configured to apply a spring force at least before the clutch element and the drivable expelling mechanism contact each other.

9. The drive train according to claim 6, wherein the at least one flexible metal element is formed as a spring having a flexible ramp profile acting axially and/or tangentially between the clutch element and the drivable expelling mechanism.

10. The drive train according to claim 1, wherein the flexible impact portion is configured as at least a compressible portion of the drivable expelling mechanism.

11. The drive train according to claim 10, wherein the compressible portion of the drivable expelling mechanism is arranged adjacent the ratchet.

12. The drive train according to claim 11, wherein the compressible portion of the drivable expelling mechanism is arranged between the clutch element and the drivable expelling mechanism.

13. The drive train according to claim 11, wherein the compressible portion of the drivable expelling mechanism is configured as a slot in an edge region of the drivable expelling mechanism.

14. The drive train according to claim 13, wherein the slot is beneath a protruding tooth of the drivable expelling mechanism.

15. The drive train according to claim 14, wherein the slot is configured so that due to impact onto the drivable expelling mechanism the tooth deflects.

16. The drive train according to claim 1, wherein the flexible impact portion is formed as a compressible pad arranged on the clutch plate of the clutch element.

17. The drive train according to claim 1, wherein the flexible impact portion is configured as a compressible nose extended from the rotatable element.

18. The drive train according to claim 17, wherein the rotatable element is a number sleeve part.

19. A wind-up injection device comprising a drive train, the drive train comprising:
a rotatable element,
a torsional spring adapted to be loaded or unloaded by the rotatable element,
a rotatable user handle coupled with a button,
a rotationally drivable expelling mechanism adapted to expel the liquid drug, and
a clutch element configured to couple to the rotatable element and comprising a ratchet for maintaining the rotatable element at one of a number of discrete angular positions against the torque of the torsional spring, wherein the clutch element is adapted to transmit a torque from the user handle via the rotatable element to the torsional spring or from the torsional spring via the rotatable element to the expelling mechanism, and wherein the ratchet is switchable from one position to an adjacent position by a torque transmitted from the user handle to the torsional spring, and wherein the drive train is adapted to dampen torque peaks by a flexible impact portion associated with the clutch element, thereby allowing softening of a possible impact between the clutch element and the expelling mechanism.

20. The wind-up injection device according to claim 19, wherein the flexible impact portion is formed as a compressible portion arranged adjacent an axial clutch bearing between the clutch element and the button.

* * * * *